(12) United States Patent
Mignon et al.

(10) Patent No.: US 8,883,918 B2
(45) Date of Patent: Nov. 11, 2014

(54) PROCESS FOR RECYCLING PRODUCT STREAMS SEPARATED FROM A HYDROCARBON-CONTAINING FEED STREAM

(75) Inventors: Denis Mignon, Braine-l'Alleud (BE); David Vandewiele, Strépy-Bracquegnies (BE); Bernard Van De Schrick, Brussels (BE); Camille Vercruysse, Ernage (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 143 days.

(21) Appl. No.: 13/392,531

(22) PCT Filed: Sep. 10, 2010

(86) PCT No.: PCT/EP2010/005562
§ 371 (c)(1),
(2), (4) Date: Mar. 23, 2012

(87) PCT Pub. No.: WO2011/029608
PCT Pub. Date: Mar. 17, 2011

(65) Prior Publication Data
US 2012/0178879 A1   Jul. 12, 2012

(30) Foreign Application Priority Data
Sep. 11, 2009  (EP) .................... 09170106

(51) Int. Cl.
*B01D 3/00* (2006.01)
*C08F 2/01* (2006.01)
*C08F 297/08* (2006.01)
*B01D 3/14* (2006.01)

(52) U.S. Cl.
CPC .................... *B01D 3/146* (2013.01)
USPC ............... 525/53; 525/54; 525/191; 525/240; 526/68; 526/69; 526/70; 526/348; 422/134; 203/71

(58) Field of Classification Search
CPC ........ B01D 3/009; B01D 3/146; C08F 2/001; C08F 297/08
USPC ......... 422/134; 525/53, 54, 240, 191; 526/68, 526/69, 70, 348
See application file for complete search history.

(56) References Cited

U.S. PATENT DOCUMENTS

| 3,642,731 A | 2/1972 | Tegge et al. |
| 4,589,957 A | 5/1986 | Sherk et al. |
| 6,045,661 A * | 4/2000 | Kreischer et al. ............... 203/73 |

* cited by examiner

*Primary Examiner* — Roberto Rabago

(57) ABSTRACT

The present invention relates to a process for recycling product streams that have been separated from a hydrocarbon-containing feed stream comprising olefin monomer, olefin co-monomer, hydrocarbon diluent and components such as $H_2$, $N_2$, $O_2$, $CO$, $CO_2$, and formaldehyde. In accordance with the present process a hydrocarbon-containing feed stream is separated into a) a first side stream comprising hydrocarbon diluent and olefin monomer; b) a second side stream which is substantially hydrogen-free and comprises hydrocarbon diluent and olefin monomer, c) a bottom stream comprising substantially olefin-free hydrocarbon diluent, and d) an overhead vapor stream comprising olefin monomer, hydrocarbon diluent and components such as formaldehyde, $H_2$, $N_2$, $O_2$, $CO$ and $CO_2$. The present process further includes recycling said first and said second side streams in a polymerization process for preparing bimodal polyolefin.

15 Claims, 2 Drawing Sheets

PROCESS FOR RECYCLING PRODUCT STREAMS SEPARATED FROM A HYDROCARBON-CONTAINING FEED STREAM

CROSS-REFERENCE TO RELATED APPLICATIONS

This application claims the benefit of PCT/EP2010/005562, filed Sep. 10, 2010, which claims priority from EP 09170106.0, filed Sep. 11, 2009.

FIELD OF THE INVENTION

The present invention relates generally to olefin polymerization. In particular, the present invention relates to a process for the separation of a hydrocarbon-containing feed stream comprising olefin monomer, one or more optional co-monomers and hydrocarbon diluent into different product streams and includes recycling of the separated product streams in a polymerization process for preparing bimodal polyolefin. The present invention thus relates to an optimization of the recycle system and process during olefin polymerisation.

BACKGROUND OF THE INVENTION

Olefin polymerizations are frequently carried out using monomer, diluent and catalyst and optionally co-monomers and hydrogen in a reactor. When the polymerization is performed under slurry conditions, the product consists usually of solid particles and is in suspension in a diluent. The slurry contents of the reactor are circulated continuously with a pump to maintain efficient suspension of the polymer solid particles in the liquid diluent. The product is discharged by means of settling legs, which operate on a batch principle to recover the product. Settling in the legs is used to increase the solids concentration of the slurry finally recovered as product slurry.

Alternatively, the product slurry may be fed to a second reactor serially connected to the first reactor where a second polymer fraction may be produced. Typically, when two reactors in series are employed in this manner, the resultant polymer product is a bimodal polymer product, which comprises a first polymer fraction produced in the first reactor and a second polymer fraction produced in the second reactor, and has a bimodal molecular weight distribution. The resultant product will also usually consist of solid particles in suspension in a diluent and will then be discharged from the second reactor using settling legs in a similar way as explained above.

The product slurry recovered in an olefin polymerization process comprises a slurry of polymer solids in a liquid that contains diluent, dissolved unreacted monomer, and optionally dissolved unreacted co-monomer. Typically this liquid also includes traces of heavier elements, e.g. oligomers, and lighter components including $H_2$, $N_2$, $O_2$, CO and/or $CO_2$. Catalyst will generally be contained in the polymer.

Once recovered from the reactor, the product slurry is discharged to a flash tank, through flash lines, where most of the diluent and unreacted monomers and optionally unreacted co-monomers are flashed off. Afterwards, it is highly desirable to further treat the vapors in order to recover the unreacted monomer, optionally unreacted co-monomer and the diluent, since there is an economic interest in re-using these separated components including the monomer, co-monomer, and the diluent, in a polymerization process.

It is known in the art that a vaporous stream comprising unreacted monomer, unreacted co-monomer and diluent issued from the effluent of a polymerization process may be treated in a distillation system for separation of its components. Traditionally, the diluent is captured through a complicated process so that such diluent can be recycled to the reactor.

U.S. Pat. No. 4,589,957 for instance describes a separation process of a hydrocarbon-containing vaporous stream comprising monomer, co-monomer and diluent issued from the effluent of a homo-polymerization and/or co-polymerization process. The described process comprises subjecting the vaporous stream to a two-stage distillation provided with a common accumulation zone wherein the condensate from the accumulation zone serves as the source of feed for the second distillation and reflux for the first distillation.

However, a problem encountered in many distillation systems, is that there is a sub-optimal separation of lighter components, including $H_2$, $N_2$, $O_2$, CO and/or $CO_2$, from recovered diluent. As a consequence, use of separated diluent streams containing these components in a polymerization process may seriously reduce polymerization efficiency and result in sub-optimal polymerization conditions. Especially in the case of re-using separated diluent streams in a polymerization process for preparing bimodal polymer product, it is for instance required to recover diluent streams wherein the residual amount of lighter components such as hydrogen, is substantially reduced in order to be able to use these diluent streams in reactors wherein the higher molecular weight component of a bimodal polymer product is prepared.

An example of a recovery process that is currently applied to meet this requirement involves the production of large amounts of diluent streams that are substantially free of olefin. However, such recovery process involves the re-utilisation of a diluent stream which is in fact too pure for that purpose as it substantially lacks olefin monomer and hence also is too costly for that use. Moreover, separation methods adapted to recover large amounts of substantially olefin-free diluent entail a number of problems and disadvantages, including inter ails requiring high amounts of energy for carrying out the separation process; resulting in increased amounts of olefin monomers that have to be separated from lighter components such as those given above; increased loss of olefin monomer, reduced stability of distillation systems; etc.

In view of the above, there remains a great need in the art for optimised methods for recycling hydrocarbon-containing feed streams that need to be separated into streams that can be recycled to a polymerization process, especially wherein bimodal polyolefins, such as for instance bimodal polyethylene, is prepared. Furthermore, there is a need in the art to provide a diluent recycle process that is less expensive to construct and/or to operate.

SUMMARY

The Applicants provide a process that overcomes at least some of the above-mentioned problems. Thereto an optimised process for separating a hydrocarbon-containing feed stream into different product streams and for re-using said separated product streams is provided. More in particular, the herein provided process permits to optimally recycle the separated streams in a polymerization process for preparing bimodal polymer.

In a first aspect, the invention thereto provides a process for recycling product streams separated from a hydrocarbon-containing feed stream comprising olefin monomer, one or more optional olefin co-monomer, hydrocarbon diluent and components such as $H_2$, $N_2$, $O_2$, CO, $CO_2$, and formaldehyde, wherein said hydrocarbon-containing feed stream is separated by the steps of:
  a) introducing said feed stream into a first distillation column for subjecting said feed to distillation conditions adapted to remove
    a1) a bottom stream comprising hydrocarbon diluent and one or more optional co-monomer, and
    a2) an overhead stream comprising hydrocarbon diluent, olefin monomer and components such as $H_2$, $N_2$, $O_2$, CO, $CO_2$, and formaldehyde;
  b) condensing the overhead stream issued from the first distillation column in step a2) to form a condensate and storing said condensate in a separator (108) adapted to separate a vapor stream and a liquid stream;
  c) removing from said separator said vapor stream comprising olefin monomer, hydrocarbon diluent and components such as formaldehyde, $H_2$, $N_2$, $O_2$, CO and $CO_2$;
  d) condensing the vapor stream removed in step c) to form a condensate and storing said condensate in a separator adapted to separate a vapor stream and a liquid stream (15);
  e) removing from said separator said liquid stream of step d);
  f) separating said liquid stream into a first side stream comprising hydrocarbon diluent and olefin monomer; and a remainder stream;
  g) introducing said remainder stream in a second distillation column and subjecting said remainder stream to distillation conditions adapted to remove
    g1) a bottom stream comprising substantially olefin-free hydrocarbon diluent,
    g2) a substantially hydrogen-free second side stream comprising hydrocarbon diluent and olefin monomer, and
    g3) an overhead vapor stream comprising olefin monomer, hydrocarbon diluent and components such as formaldehyde, $H_2$, $N_2$, $O_2$, CO and $CO_2$.

In accordance with the present method, it is further noted that vapor stream issued from the separator of the first distillation column is sent/fed to the overhead condenser of the second distillation column. The present invention is thus characterized in that it comprises at least two condensation/separation cycles provided in series. This advantageously permits to limit monomer loss, and therefore to reduce production costs. In particular, in the case of polyethylene production, such mode of operation allows to limit the loss of ethylene with the ethane purge in case of bimodal configuration of the reactors. In another embodiment of the present process, a portion of the condensate stored in step b) is removed as liquid stream and passed as reflux to the first distillation column.

In a preferred embodiment, the invention provides a process wherein said first and said second side streams are recycled in a polymerization process for preparing bimodal polyolefin comprising at least two different polyolefin fractions that have been obtained in two different polymerisation reactors connected to each other in series, and wherein one of said fractions has a higher molecular weight than said other fraction, and wherein said second side stream is re-used in the polymerization process wherein the polyolefin fraction having the higher molecular weight is prepared, and wherein said first side stream is re-used in the polymerization process wherein the other polyolefin fraction is prepared.

In other words, the present process involves the steps of recycling said first and said second side streams in a polymerization process for preparing bimodal polyolefin comprising at least two different polyolefin fractions that have been obtained in two different polymerisation reactors connected to each other in series, and wherein one of said fractions has a higher molecular weight than said other fraction. The second side stream is re-used in the polymerization process wherein the polyolefin fraction having the higher molecular weight is prepared and the first side stream is re-used in the polymerization process wherein the other polyolefin fraction, i.e. the polyolefin fraction having the lower molecular weight, is prepared. The first side stream can thus be fed to a reactor in which the polyolefin fraction having the higher molecular weight is prepared, while the second side stream can be fed to the reactor in which said other polyolefin fraction is prepared.

In yet another embodiment, the invention provides a process in which said bottom stream of step g1) is re-used in a polymerization process for preparing bimodal polyolefin comprising at least two different polyolefin fractions that have been obtained in two different polymerisation reactors connected to each other in series, and wherein one of said fractions has a higher molecular weight than said other fraction, and wherein said bottom stream is re-used in the polymerization process wherein the polyolefin fraction having the higher molecular weight is prepared.

In another embodiment, the invention provides a process comprising the steps of
  h) condensing the overhead vapor stream obtained in step g3 optionally in admixture of the vapor stream removed in step c) to form a condensate, and storing the condensate thus formed in a separator; and
  i) subjecting the stored condensate obtained in step h) to steps e) to g).

Preferably, the process further comprises the step of removing from the condensate stored in step d) a vapor stream comprising olefin monomer, and components such as formaldehyde, $H_2$, $N_2$, $O_2$, CO and $CO_2$; and recovering olefin monomer from said vapor stream.

In yet another embodiment, the present invention provides a process which may further comprise the step of introducing the bottom stream of step a1) in a third distillation column (3) for subjecting said bottom stream to distillation conditions adapted to remove 1) a side stream comprising one or more optional co-monomer, 2) an overhead stream comprising hydrocarbon diluent and optionally co-monomer, and 3) a bottom stream comprising heavy components.

Preferably the side stream 1) is taken from the lower part of the distillation column e.g. from tray 3 of the column, when counting from the bottom of the column. Generally, the overhead stream of the third distillation column will contain only minor amounts of co-monomer.

This overhead stream of the third distillation column comprising hydrocarbon diluent can be fed back to the first distillation column. Preferably, the overhead stream which exits the top of the third distillation column is first cooled down in an overhead condenser of the third distillation column. Then the condensed stream, issued at the outlet of the condenser of the third distillation column is collected in a reflux drum of the third distillation column. The condensate can then be split up in two parts: a first part thereof is sent as reflux to the third distillation column and a second part is recycled as feed to the first distillation column.

Alternatively or in combination therewith, bottom stream of step a1) can also advantageously be re-used in the polymerization process for preparing bimodal polyolefin. Especially it can be fed to the reactor in which the polyolefin fraction with the higher molecular weight fraction is prepared. In bimodal configuration, the reactor in which the polyolefin fraction with the higher molecular weight fraction is prepared is also the one in which co-monomer (e.g. hexene) concentration is the highest.

It shall be noted that all values that are given herein in ppm are meant to refer to values of ppm by weight. Hence the terms "ppm" and "ppm by weight" are used herein as synonyms.

In another embodiment, the present invention provides a process wherein said first side stream of step f) comprises at least 3 wt %, more preferably at least 5 wt % olefin monomer. In another embodiment, the present invention provides a process wherein said first side stream of step f) comprises less than 10 wt % olefin monomer, and for instance less than 8 wt % olefin monomer.

In another embodiment, the present invention provides a process wherein said first side stream of step f) comprises between 100 and 10000 ppm by weight hydrogen, preferably between 100 to 5000 ppm by weight. In a preferred embodiment said first side stream of step f) comprises less than 500 ppm by weight hydrogen.

In still another embodiment, the invention provides a process wherein said second side stream of step g2) is removed from the upper third of said second distillation column. In an embodiment, the present invention provides a process wherein said second side stream of step g2) comprises at least 2 wt % olefin monomer, preferably at least 2.5 wt %, and more preferably at least 3 wt % olefin monomer. In another embodiment, the present invention provides a process wherein said second side stream of step g2) comprises at most 5 ppm by weight, preferably at most 2 ppm by weight, more preferably at most 1 ppm by weight hydrogen.

In yet another embodiment, the present invention provides a process wherein said bottom stream of step g1) comprises less than 5 ppm by weight of olefin monomer, and preferably less than 1 ppm by weight of olefin monomer. In another embodiment, the present invention provides a process wherein said bottom stream of step g1) comprises less than 5000 ppm by weight of olefin co-monomer.

In another preferred embodiment, a process is provided wherein said hydrocarbon-containing feed stream comprising olefin monomer, co-monomer and hydrocarbon diluent is an effluent stream obtained from a polymerization process for preparing monomodal or bimodal polyolefin. Preferably, said olefin monomer is ethylene, said co-monomer is 1-hexene and said hydrocarbon diluent is isobutane.

The present process includes the recovery of a side stream which is substantially free of hydrogen. This side stream is as rich as possible in olefin monomer while still poor enough in hydrogen, so that it can be fed to the reactor wherein the polymer fraction having the higher molecular weight is prepared during a bimodal polymerisation process. Consequently, the need for using an olefin-free hydrocarbon stream for that same purpose is strongly reduced. Since the flow rate of steam used for reboiling the distillation column is directly proportional to the flow rate of olefin-free hydrocarbon stream to be obtained as bottom stream, reducing this bottom stream further makes it possible to significantly reduce the steam consumption necessary to ensure proper re-boiling of the distillation column.

Another advantage of the present invention is that said substantially hydrogen-free side stream will take up olefin monomer, and hence significantly reduce—e.g. by more than 50%—the incondensable vaporous stream which contains the main part of the hydrogen entering the recycle section and which is removed from the recycle section and sent to a monomer recovery unit. Hence, the present invention permits to recover a larger portion of the olefin monomer entering the recycle section before it is sent to a recovery unit compared to currently applied recovery processes. For instance, the present invention permits to recover a larger portion of ethylene monomer entering the recycle section before it is sent to an ethylene recovery unit (ERU) compared to currently applied recovery processes. In accordance with the present process, recovering a substantially hydrogen-free side stream from the hydrocarbon feed stream permits to significantly reduce the loss of ethylene monomer.

Further in accordance with the present process less incondensable vaporous stream containing lighter components needs to be sent to the monomer recovery unit and the size of the monomer recovery unit, for instance an ethylene recovery unit, can be significantly reduced. This has important economic and environmental repercussions and benefits.

Furthermore, unexpectedly, the Applicants have seen that the present process involving the recovery of a) a first side stream comprising hydrocarbon diluent and olefin monomer; b) a second side stream which is substantially hydrogen-free and comprises hydrocarbon diluent and olefin monomer, c) a bottom stream comprising substantially olefin-free hydrocarbon diluent, and d) an overhead vapor stream comprising remaining olefin monomer, remaining hydrocarbon diluent and remaining components such as formaldehyde, $H_2$, $N_2$, $O_2$, CO and $CO_2$ has improved efficiency and stability compared to conventional distillation system which lack recovery of said second side stream.

The present optimized recovery process is particularly suitable for providing diluents streams for re-use in a polymerization system for preparing bimodal polymer product. In particular, the present invention provides a process enabling to separately recover I) a substantially hydrogen-free diluent side stream that can be used in the reactor wherein the higher molecular weight fraction of a bimodal polymer is prepared; and II) a diluent side stream that can be used in the reactor wherein the lower molecular weight fraction of a bimodal polymer is prepared. Thus the present process optimally provides two side streams that each can be re-used to feed diluent to the respective reactors applied in the polymerization process for preparing bimodal polyolefins, for instance bimodal polyethylene.

In another aspect, the invention therefore also relates to the use of a process according to the invention in a polymerization process for preparing bimodal polyolefin, such as for instance bimodal polyethylene, comprising at least two different polyolefin fractions that have been obtained in two different polymerisation reactors connected to each other in series, and wherein one of said fractions has a higher molecular weight, comprising the steps of:

feeding olefin monomer, a diluent, at least one polymerization catalyst, optionally hydrogen, and one or more optional olefin co-monomer(s) to a first reactor,
  polymerizing said olefin monomer in said first reactor to produce a polymer slurry comprising a first polyolefin fraction in the diluent,
  transferring said polymer slurry from said first reactor to a second reactor,
  feeding olefin monomer, a diluent, optionally hydrogen, and one or more optional olefin co-monomer(s) to said second reactor,
  polymerizing said olefin monomer and said one or more optional olefin co-monomer(s) in said second reactor to produce a slurry comprising a second polyolefin fraction in the diluent, said second polyolefin fraction having a different molecular weight than the polyolefin fraction produced in said first reactor, and discharging from said second reactor a slurry comprising bimodal polyolefin in said diluent, recovering bimodal polyolefin from the slurry by separating at least a majority of the diluent from the slurry in a hydrocarbon-containing feed stream, and subjecting said hydrocarbon-containing feed stream to a process as described herein.

In yet another aspect, the invention also provides a polymerization system for preparing bimodal polyolefin comprising two polymerisation reactors connected to each other in series operably connected to a distillation system, the distillation system comprising a first distillation column and a second distillation column which are operably connected to each other in series; and wherein said first distillation column which is configured to separate a hydrocarbon-containing feed stream comprising olefin monomer, optionally one or more co-monomer and hydrocarbon diluent, into a bottom stream comprising hydrocarbon diluent and one or more optional co-monomer, and an overhead stream comprising hydrocarbon diluent, olefin monomer and components such as $H_2$, $N_2$, $O_2$, $CO$, $CO_2$, and formaldehyde;

is provided with at least one condenser for condensing said overhead feed stream to form a condensed stream and at least one separator, operably connected to said condenser and adapted to separate said condensed stream in a vapor stream and a liquid stream; and wherein said second distillation column which is configured to separate a hydrocarbon-containing feed stream comprising olefin monomer, optionally one or more co-monomer and hydrocarbon diluent, into a bottom stream comprising substantially olefin-free hydrocarbon diluent, a substantially hydrogen-free side stream comprising hydrocarbon diluent and olefin monomer, and an overhead stream comprising olefin monomer, hydrocarbon diluent and components such as formaldehyde, $H_2$, $N_2$, $O_2$, $CO$ and $CO_2$, is provided with at least one condenser for condensing said overhead stream to form a condensed stream and at least one separator, operably connected to said condenser and adapted to separate said condensed stream in a vapor stream and a liquid stream, of which a part is separated as a first side stream comprising hydrocarbon diluent and olefin monomer.

The present invention will be further disclosed in detail hereunder. The description is only given by way of example and does not limit the invention. The reference numbers relate to the hereto-annexed figures.

DETAILED DESCRIPTION OF THE INVENTION

Figure 1:
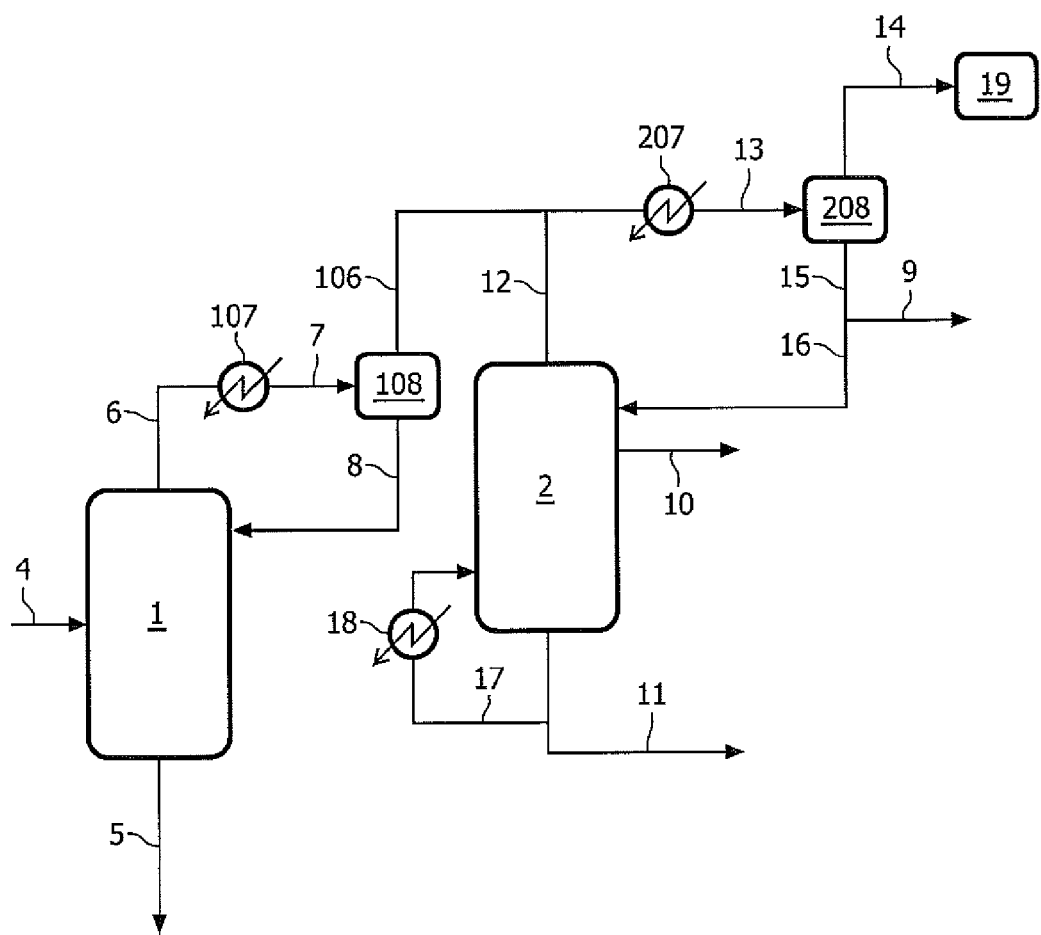
FIG. 1 represents a schematic view of an embodiment of a distillation system comprising two distillation columns according to the present invention.

The present invention is directed to a process for separating a hydrocarbon-containing feed stream comprising olefin monomer, one or more optional olefin co-monomers, hydrocarbon diluent and components such as $H_2$, $N_2$, $O_2$, $CO$, $CO_2$, and formaldehyde in different product streams and further comprises recycling the separately recovered product streams in a polymerization process, preferably for preparing bimodal polymer. The present process is optimized in terms of separation into different product streams and in terms of recycling of the separated streams, in particular by controlling or re-distributing the amounts of recovered product streams and the concentrations of reactants within said recovered streams.

The hydrocarbon-containing feed stream that is separated according to the present invention will generally be an overhead stream coming from a flash tank and purge columns of a polymerization reactor, wherein a stream containing solvent/diluent, polymer and unreacted monomers is flashed or otherwise treated to remove solvent or diluent and monomers there from.

In another embodiment said hydrocarbon-containing feed stream can be an overhead stream coming from another distillation column.

The hydrocarbon-containing feed stream that is separated and recycled according to the present invention can be obtained from any polymerization process producing an effluent comprising a slurry of particulate polymer solids suspended in a liquid medium comprising a diluent and unreacted monomer. Such reaction processes include those which are known in the art as particle form polymerizations, also referred to as slurry polymerization.

As used herein, the term "polymerization slurry" or "polymer slurry" or "slurry" means substantially a two-phase composition including polymer solids and liquid. The solids include catalyst and a polymerized olefin, such as polyethylene. The liquids include an inert diluent, such as isobutane, with dissolved monomer such as ethylene, optionally co-monomer, such as 1-hexene, molecular weight control agents, such as hydrogen, antistatic agents, antifouling agents, scavengers, and other process additives.

In a preferred embodiment, the present invention is directed to the separation process of a vaporous stream, which is issued from the effluent of an ethylene polymerization reaction. Suitable "ethylene polymerization" includes but is not limited to homo-polymerization of ethylene, and co-polymerization of ethylene and a higher 1-olefin co-monomer such as butene, 1-pentene, 1-hexene, 1-octene or 1-decene. A presently preferred component stream separated according to the invention comprises monomer, such as ethylene, co-monomer, such as 1-hexene, and diluent, such as isobutane. It should be recognized however, that the distillation system of the invention is equally applicable to other monomer, co-monomer and diluent systems so long as feed vapors comprise hydrocarbons, which permit separation by distillation. Traces of both heavy components, e.g. oligomers, and lighter components such as formaldehyde, $N_2$, $H_2$, and components such as $O_2$, $CO$ and $CO_2$ are generally also present in such effluent streams.

More in particular, the present invention relates to a separation process of a hydrocarbon-containing feed, wherein said hydrocarbon-containing feed stream is an effluent stream obtained from a polymerization process for preparing monomodal or bimodal polyolefins, such as monomodal or bimodal polyethylene (PE), and preferably for preparing bimodal polyethylene. "Bimodal PE" refers to PE that is manufactured using two reactors, which are connected to each other in series, the operating conditions being different in the two reactors. "Monomodal PE" is produced in a single reactor or using two reactors in series, with identical operating conditions.

The term "separation" as used herein refer to the step of fractionating a hydrocarbon-containing feed stream in different fractions, which can than be re-used.

Further, in accordance with the present process the product streams separated from said hydrocarbon-containing feed stream are recycled in an olefin polymerization process, preferably in an ethylene polymerization process, and more preferably in a polymerization process for preparing bimodal polyolefins, such as bimodal polyethylene.

The terms "bimodal polyolefin product" or "bimodal polyolefin" as used in the present invention are meant to designate polymer products comprising at least two fractions of olefin polymer wherein one fraction has a lower molecular weight than the other fraction. The terms "bimodal polyethylene product" or "bimodal polyethylene" as used in the present invention are meant to designate polymer products comprising at least two fractions of ethylene polymer wherein one fraction has a lower molecular weight than the other fraction. Bimodal polyolefins, such as bimodal PE can be produced in a sequential step process, utilizing polymerization reactors coupled in series and using different conditions in each reactor, the different fractions produced in the different reactors will each have their own molecular weight.

In an embodiment a polymerization process for preparing bimodal polyolefin, such as bimodal polyethylene, is carried out in a double loop polymerization reactors unit consisting of two liquid full loop reactors, comprising a first and a second reactor connected in series by one or more settling legs of the first reactor connected for discharge of slurry from the first reactor to said second reactor. The first polyolefin fraction, diluent and catalyst can be continuously or discontinuously transferred from said first reactor to said second reactor.

More in particular, in an embodiment, a first polyolefin, e.g. a first polyethylene fraction is obtained by a first polymerisation process of olefin monomer, such as e.g. ethylene, in a diluent, such as e.g. isobutane, in the presence of a catalyst. Such first polymerisation process comprises the steps of feeding olefin monomer, a diluent, at least one polymerization catalyst, optionally hydrogen, and one or more optional olefin co-monomer(s), such as e.g. 1-hexene, to said first reactor, and polymerizing said olefin monomer in said first reactor to produce a first polyolefin fraction, diluent and catalyst is transferred from said first reactor to a second reactor. In the second reactor a second polyolefin fraction is obtained by feeding olefin monomer, such as e.g. ethylene, a diluent, such as e.g. isobutane, optionally hydrogen, and one or more optional olefin co-monomer(s), such as e.g. 1-hexene, to said second reactor; polymerizing said monomer and said one or more optional olefin co-monomer(s) in said second reactor to produce a second polyolefin fraction in said second reactor. Said second polyolefin fraction has a different molecular weight than the polyolefin fraction produced in said first reactor. From the second reactor bimodal polyolefin product comprising said first and said second polyolefin fraction is then recovered. This bimodal polyolefin product is then supplied, optionally in combination with one or more additives to an extruder.

In a particularly preferred embodiment of the above method, said second polyolefin fraction produced in said second reactor has a lower molecular weight than said first polyolefin fraction produced in said first reactor. In another preferred embodiment, hydrogen is added to the second reactor wherein the second polyolefin fraction is produced having a lower molecular weight than said first polyolefin fraction.

In a preferred embodiment, a first polyethylene fraction prepared in a first reaction is a high-molecular-weight (HMW) component, composed of an ethylene homopolymer or copolymer, for instance with a weight-average molar mass ≥300,000 g/mol, preferably from 300,000 to 700,000 g/mol and very particularly preferably from 300,000 to 600,000 g/mol, and preferably having a higher molecular weight than the second polyethylene fraction. In another preferred embodiment, a second polyethylene fraction prepared in a second reaction is a low-molecular-weight (LMW) component, composed of an ethylene homopolymer or ethylene copolymer, for instance with a weight-average molar mass of from 8000 to 80,000 g/mol, preferably from 20,000 to 70,000 g/mol and very particularly preferably from 30,000 to 60,000 g/mol, and preferably having a lower molecular weight than the first polyethylene fraction.

The term "recycling" or "re-use" are used in the present invention herein as synonyms and both refer to the step of sending or feeding a product stream that has been separated from a hydrocarbon-containing effluent stream back to a polymerization reactor for use therein.

Separation of a hydrocarbon-containing feed stream—also denoted hydrocarbon-containing effluent stream—into different separated product streams is carried in a distillation system. The terms "distillation system" or "separation system", "recovery system" or "recycle section", are used in some embodiments of the present invention as synonyms and refer to systems comprising all necessary equipment adapted to separate and recover unreacted reactants from the effluent stream of a polymerization reaction. Such recovery systems generally include one or more distillation columns. The term "distillation zone", "separation column" and "distillation column" may be used herein as synonyms. In a preferred embodiment, the present distillation process is carried out in a distillation system, which comprises one or more distillation columns, e.g. two or three distillation columns.

In a preferred embodiment, one or more of said distillation columns are tray columns. Such tray columns comprise a number of trays of various designs to hold up the liquid in order to provide better contact between vapor and liquid. Trays essentially act as a unit operation, each accomplishing a fraction of the separation between liquid and gas. It is clear that the more trays there are, the better the degree of separation, and thus the better column performance will be. However, using a large number of trays in distillation columns has important disadvantages, especially with regard to construction. Suitable distillation systems comprise distillation system having column(s) with a low number of trays, preferably lower than 25, even more preferred lower than 20. Nevertheless, although distillation columns with a low number of trays can be used in the present process, improvements on the operation of the present distillation systems, as explained in more detail below, permit to achieve a similar degree of separation as with columns with a higher number of trays. Advantageously, application of the present process includes the benefits of less energy usage and lower construction costs.

In an alternative embodiment, one or more of said distillation columns are divided wall distillation columns. Such a column is a distillation vessel having a vertical partition separating one side from the other for a portion of the height of the vessel. Although such column comprises a larger number of trays, the use of such single column may be advantageous with regard to construction costs and energetic requirements.

In a preferred embodiment, one or more of said distillation columns are packing columns. Packing column refers to a column packed with inert solid particles.

Reboilers are used as heat exchangers to provide heat to the bottom of said distillation columns. They boil the liquid from the bottom of a distillation column to generate vapors which are returned to the column to drive the distillation separation. The reboiler receives a liquid stream from the column bottom and may partially or completely vaporize that stream. Steam usually provides the heat required for the vaporization. In accordance with the present invention, a portion of the bottom stream obtained in the distillation column is reboiled and said re-boiled portion is returned to the distillation column.

In accordance with the present invention, separate streams of monomer, optionally co-monomer, and diluent are recycled for further use. The vaporous feed stream to be separated, coming e.g. from the flash tanks, also comprises traces of both heavy components, e.g. oligomers, and lighter components including $N_2$, $H_2$, and light poisonous components such as $O_2$, CO and $CO_2$, and formaldehyde. Such components are herein also denoted as "poisonous components", because such components are detrimental for the activity of a catalyst. Re-introduction thereof into a polymerization reactor could greatly disturb catalyst activity and thus reduce polymerization efficiency. It is therefore of the utmost importance to have a recovery system adapted to recover streams of (co-) monomer, and diluent, having residual amounts of such poisonous components which are appropriate depending on their conditions of re-use in a polymerization process, e.g. depending on the reactor wherein they are fed in a bimodal system.

In accordance with the present invention, different diluent-containing product streams are separated from the feed stream and can be re-used in a polymerization process for preparing bimodal polymer. More in particular, in accordance with the present invention, said hydrocarbon-containing feed stream is separated into I) a bottom stream comprising substantially olefin-free hydrocarbon diluent;

II) an overhead vapor stream comprising olefin monomer, hydrocarbon diluent and components such as formaldehyde, $H_2$, $N_2$, $O_2$, CO and $CO_2$;

III) a first side stream comprising hydrocarbon diluent and olefin monomer; and

IV) a second side stream which is substantially hydrogen-free and comprises hydrocarbon diluent and olefin monomer.

According to a particular embodiment of the present invention the hydrocarbon-containing feed stream is condensed before being separated into the product streams given above.

In another preferred embodiment said hydrocarbon-containing feed stream comes as an overhead vapour stream from another (first) distillation column, wherein the feed has been subjected to distillation conditions adapted to remove a1) a bottom stream comprising hydrocarbon diluent and one or more optional co-monomers, and a2) an overhead stream comprising hydrocarbon diluent, olefin monomer and components such as $H_2$, $N_2$, $O_2$, CO, $CO_2$, and formaldehyde.

More in particular, preferably, said overhead vapour stream obtained in step a2) is subjected to the following steps before being condensed by the overhead condenser of a second distillation column:

the overhead stream issued from the first distillation column is condensed to form a condensate and the thus formed condensate is stored in a reflux drum (a first separator) of the first distillation column; the reflux drum is adapted to separate a vapor stream and a liquid stream;

the vapor stream is removed from said first separator, the vapor stream is condensed to form a condensate and stored in a second separator adapted to separate a vapor stream and a liquid stream;

the liquid stream is removed from said second separator and this liquid stream is separated into a first side stream and a remainder stream;

the remainder stream is introduced in a second distillation column and subjected to distillation conditions In other words, from said reflux drum of the first distillation column (first separator) a portion of the stored condensate is removed as liquid stream and fed to the first distillation column; while another portion of the stored condensate is removed from the separator as vapour stream. This vapour stream comprises olefin monomer, hydrocarbon diluent and components such as formaldehyde, $H_2$, $N_2$, $O_2$, CO and $CO_2$. It is the latter vapour stream that is then again condensed by the overhead condenser of a second distillation column to form a condensate and then stored in a reflux drum of the second distillation column before being separated into the product streams given above.

The bottom stream (I) comprises substantially olefin-free hydrocarbon diluent. The term "substantially olefin-free hydrocarbon diluent" or "olefin-free diluent" or the like are used herein as synonyms to denote hydrocarbon diluent which contains less than 5 ppm by weight, and preferably less than 1 ppm by weight of monomer; and less than 5000 ppm by weight, preferably less than 1000 ppm by weight and more preferably less than 100 ppm by weight of optional co-monomer. This bottom stream is also substantially free of hydrogen, and in particular contains only traces of hydrogen, for instance less than $10^{-2}$ ppm, preferably less than $10^{-3}$ ppm of hydrogen. Substantially free of traces of monomer such as ethylene and/or optional co-monomer such as hexene, and of lighter components such as hydrogen, the bottom stream of olefin free hydrocarbon diluent, such as isobutane, issued from the distillation column can be sent to a storage tank and further used, e.g. for flushing conduits and circulation pumps in a polymerization reactor, or for catalyst preparation e.g. in mud pots. This olefin-free diluent can also be recycled to a polymerization zone, whether homo-polymerization or co-polymerization, at any place of the process where pure diluent is requested, like the catalyst dilution. When recycled in a bimodal polymerization process according to the present invention, this bottom stream is fed to said reactor in which the polyolefin fraction having the higher molecular weight is prepared. In accordance with the present process it is possible to reduce the amount of this bottom stream.

Light components such as formaldehyde, $H_2$, $N_2$, $O_2$, CO and $CO_2$ exit the (second) distillation column with some residual monomer and diluent as an overhead vapor stream (II). This overhead vapor exits at the top of the distillation column. The overhead stream is preferably condensed to form a condensate and is then stored. For instance this condensate is passed to a separator, also denoted reflux drum or condensate vessel herein. A portion of this stored condensate is removed, e.g. it is removed from a separator, as vapor stream comprising olefin monomer, and components such as formaldehyde, $H_2$, $N_2$, $O_2$, CO and $CO_2$; and send to an Monomer Recovery Unit, such as for instance an ethylene recovery unit (ERU) in the event of using ethylene monomer. These light components are then further treated in the Recovery Unit, which further separates the light components from the remaining monomer and hydrocarbon diluent. Preferably, the amount of remaining monomer that is sent to a monomer recovery unit is lower than 30%, preferably lower than 20%, preferably lower than 10%. Monomer and diluent that are recovered by means of the recovery unit are preferably re-used in the polymerization process.

In an example, under prior art conditions, the stream conveyed to an ethylene recovery unit (ERU) comprises isobutane, ethylene, hydrogen, nitrogen and ethane. Ethylene and isobutane are further recovered in ERU. Using the process of the invention allows reducing the amount of ethylene sent to the ERU, since ethylene monomer is recovered in an additional side stream (IV) separated from the column. Preferably, the amount of remaining ethylene that is sent to the ERU is lower than 30%, preferably lower than 20%, preferably lower than 10%.

The side stream (III) of hydrocarbon diluent issued from the distillation column is generally sent to a storage tank and further used. Preferably, the amount of further components such as $H_2$, $N_2$, $O_2$, CO and $CO_2$, formaldehyde in the side stream is preferably lower than 500 ppm, and for instance comprised between 50 and 500 ppm. In another preferred embodiment, the amount of monomer remaining in the side stream is lower than 10 wt %, for instance comprised between 5 and 10 wt %. High amounts of monomer in the storage tank of the side-stream product may lead to evaporation and substantial monomer loss. By keeping the amount of monomer in the side-stream product below 10%, evaporation of monomer from the storage tank can be reduced and storage of the side-stream product at atmospheric conditions becomes possible.

The hydrocarbon diluent issued as side stream exiting from the distillation column is in accordance with the present invention recycled and used as diluent in a polymerization process for preparing bimodal polyolefin, and preferably it can be fed to that polymerization reactor in which the polyolefin fraction with the lower molecular weight is prepared, e.g. a second reactor.

Also the side stream (IV) of hydrocarbon diluent issued from the distillation column is generally sent to a storage tank and further used. This second side stream is substantially hydrogen-free and comprises hydrocarbon diluent and olefin monomer. The term "substantially hydrogen-free" or "substantially hydrogen-free hydrocarbon diluent" or the like are used herein as synonyms to denote hydrocarbon diluent which contains less than 5 ppm by weight, and preferably less than 1 ppm by weight, and even more preferred less than 0.5 ppm by weight hydrogen. In another preferred embodiment, the amount of monomer remaining in the second side stream is lower than 5 wt %, for instance between 2 to 5 wt %.

The hydrocarbon diluent issued as second side stream exiting from the distillation column is in accordance with the present invention recycled and used as diluent in a polymerization process for preparing bimodal polyolefin, and preferably it can be fed to that polymerization reactor in which the polyolefin fraction with the higher molecular weight is prepared, e.g. a first reactor.

In a preferred embodiment, a process is provided wherein said second side stream is removed from the upper third of said second distillation column. The Applicants have shown that removing a side stream from this part of the column provides a side stream has the most optimal composition for being recycled in a reactor in which the polyolefin fraction with the higher molecular weight is prepared, e.g. a first reactor. In another embodiment, the present process is carried out in a distillation system, which comprises one or more tray distillation columns. In an example, in the case of using a distillation column having 20 trays, the process provides that the second side stream is removed from a tray of said distillation column which is selected from the upper $2^{nd}$ to $7^{th}$ tray, preferably from the upper $3^{rd}$ and $6^{th}$ tray in said distillation column. With "upper" in this context is meant as counted from the top of said distillation column.

In one embodiment, the present process is carried out in a distillation system, which comprises two distillation columns.

In yet another embodiment, the present process is carried out in a distillation system, which comprises three distillation columns.

Referring now to the figures, a recycling unit according to an embodiment of the invention is schematically illustrated in FIG. 1. The illustrated recycling section is composed of two distillation columns 1, 2 and of an monomer recovery unit represented by the box 19. The distillation columns preferably are tray columns. The hydrocarbon-containing feed stream 4 that will be separated will generally be an overhead stream coming from a flash tank and purge columns of a polymerization reactor (not shown). A first distillation column 1 realizes a rough cut between a mixture of diluent such as isobutane, comonomer such as hexene and the heavies, which exit as liquid bottom product 5. The heavy bottom product 5 can be further treated (not shown). The remaining monomer, together with some diluent and all light components, exits from the top of the first distillation column 1 as a vapor stream 6 for further separation. This overhead stream 6 from the first distillation column 1 is cooled down in an overhead condenser 107. The stream 7 at the outlet of the condenser is collected in a reflux drum 108. The reflux drum 108 is adapted to separate the stream 7 into a liquid stream 8 and a vapor stream 106. The liquid stream 8 from the reflux drum is used as reflux to the first distillation column 1 and the vapor stream 106 obtained at the outlet of the reflux drum 108 is sent to a second distillation column. However, this vapor stream 106 is not directly fed to the second distillation column as such but it is first condensed in an overhead condenser 207. The overhead condenser 207 of the second distillation column 2 thus receives the vapor stream 106 from the reflux drum 108 of the first distillation column 1 and optionally also an overhead stream 12 of the second distillation column (to be described later). Thus an overhead stream 12 to be described later is combined with stream 106 for passage through a condenser 207 and introduction in a separator 208. The stream 13 at the outlet of the condenser 207 of the second distillation column is collected in a reflux drum 208, preferably different from the reflux drum of the first distillation column described above. This reflux drum 208 is adapted to separate a liquid stream 15 and a vapor stream 14. The liquid stream is removed from the reflux drum 208 of the second distillation column 2 and is then split (separated) into a first side stream 9 comprising hydrocarbon diluent and olefin monomer; and a remainder stream 16. The remainder stream 16 is used as reflux to the second distillation column 2. In other words, a part of the liquid condensate 15 comprising monomer, diluent and lighter components such as formaldehyde, $N_2$, $H_2$, and components such as $O_2$, CO and $CO_2$ is passed from the condensate vessel 208 as feed to the second distillation column 2.

Diluent, lighter components such as $H_2$ and residual amounts of monomer, are removed as a liquid side stream 9 from the condensate vessel 208. This side stream 9 can be introduced into a storage vessel for storage and further handling. Preferably this side stream comprises less than 10 wt % monomer and less than 500 ppm by weight hydrogen. This first side stream 9 is usually recycled in a polymerization reactor. Preferably when this stream 9 is recycled in a polymerization process for preparing bimodal polyolefin comprising at least two different polyolefin fractions that have been obtained in two different polymerisation reactors connected to each other in series, and wherein one of said fractions has a higher molecular weight than said other fraction, it is re-used in the polymerization process wherein the other polyolefin fraction is prepared. The vapor stream 14 separated from the reflux drum 208 of the second distillation column 2 is further cooled down in a vent condenser (not shown), before being sent to a monomer recovery unit 19 where monomer is recovered and lights components such as $H_2$ and $N_2$ are sent to the flare.

Conditions within the distillation column 2 are such that different product streams will be generated. Substantially pure diluent, so-called "substantially olefin-free" diluent is obtained as liquid bottom product 11. This bottom stream 11, which comprises diluent substantially free of olefin monomer, is removed from a lower portion of the distillation column 2. This bottom stream can be passed through a water-cooled heat exchanger (not shown), and introduced into vessel (not shown) for storage and further handling. The second distillation column 2 further comprises devices for providing re-boiling of a portion of the bottom stream 11 under a controlled steam flow rate. For instance, according to the invention a portion of bottom stream 11 is passed through a steam-heated heat exchanger 18 and returned to the distillation column by way of line 17. Remaining diluent exits the column 2 as a second liquid side stream 10, which is substantially hydrogen-free. According to a preferred embodiment, this side stream 10 is removed from an upper third part of the distillation column 2 by way of a line (not shown) and introduced into vessel (not shown) for storage and further handling, e.g. from the $3^{rd}$, $4^{th}$, $5^{th}$ or $6^{th}$ upper tray in said distillation column 2. Light components such as formaldehyde, $H_2$, $N_2$, $O_2$, CO and $CO_2$ exit the distillation column 2 with olefin monomer and some residual diluent as a vapor stream 12, which according to another embodiment of the invention can be further condensed by a condenser 207. The condensed vapor stream 13 is then sent to the separator 208.

An incondensable vapor stream 14 is separated from the separator 208, passed through a vent condenser (not shown) for recovery of most of the entrained diluent, and then further treated in an olefin monomer recovery unit 19.

The distillation process in the second distillation column thus permits to separate substantially olefin-free diluent in a bottom stream 11 as well as diluent containing residual amounts of olefin monomer and a low amount of hydrogen, e.g. less than 5 ppm, in a side stream 10 and also diluent containing residual amounts of olefin monomer and some higher amounts of hydrogen in a side stream 9. Both the substantially olefin-free diluent 11 and the diluent 10 can be recycled and re-used in a polymerization process for preparing bimodal polyolefin, in particular in the reactor in which the polyolefin fraction having the higher molecular weight is prepared. Also the diluent 9 can be recycled and re-used in a polymerization process of preparing bimodal polyolefin, in particular in the reactor in which the polyolefin fraction having the lower molecular weight is prepared. In a particularly preferred embodiment, the monomer recovery unit 19 can be avoided. The separation of side stream 10 comprising monomer and diluent decreases dramatically the stream 14, leading to a competitive process in terms of monomer recovery without the need of having a monomer recovery unit.

Figure 2:
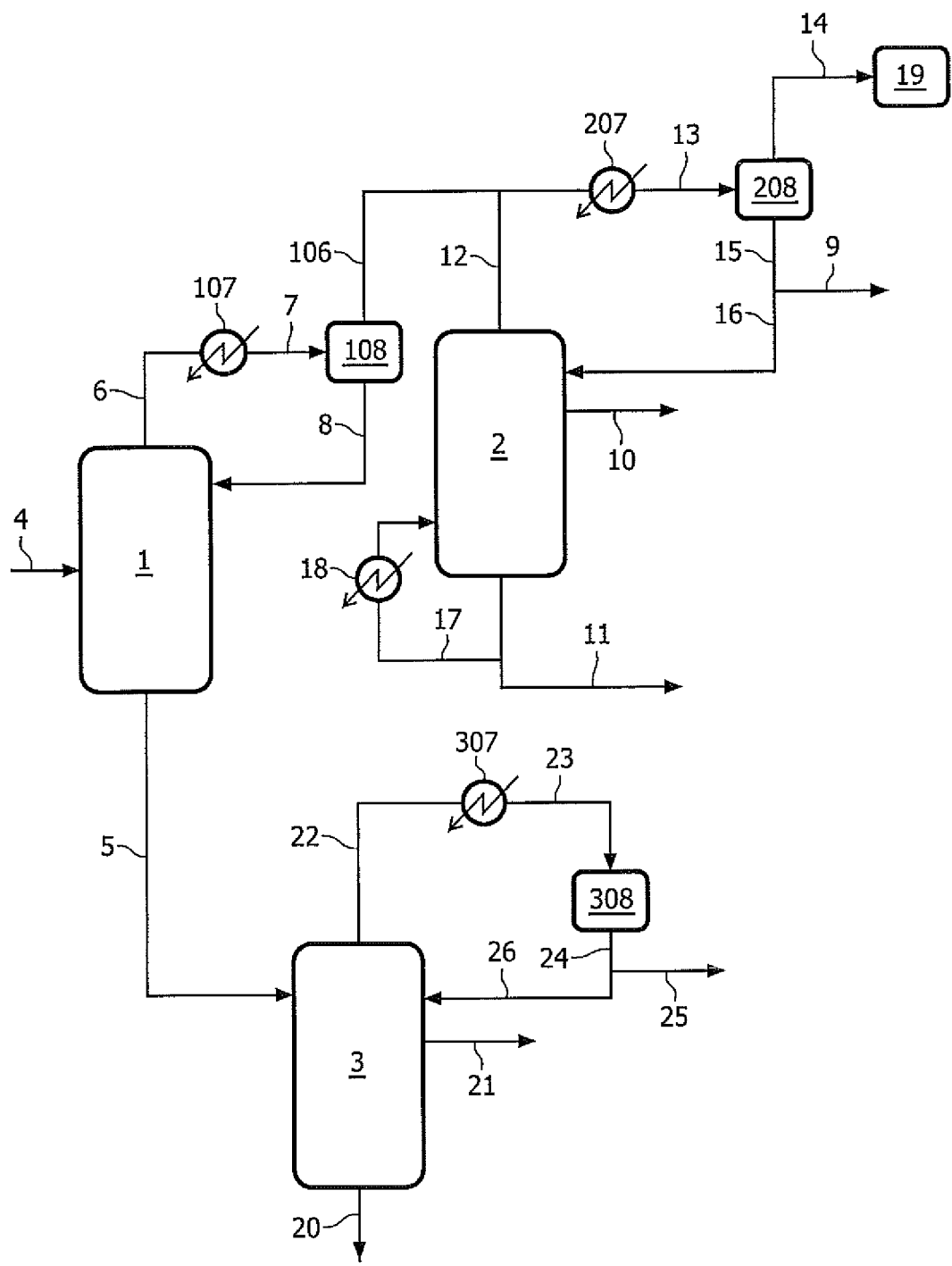
FIG. 2 represents a schematic view of an embodiment of a distillation system comprising three distillation columns according to the present invention.

As illustrated in FIG. 2, a recycling unit according to an embodiment of the invention can be composed of three distillation columns 1, 2, 3, in addition to a monomer recovery unit represented by the box 19. The hydrocarbon-containing feed stream 4 that is to be separated will generally be an overhead stream coming from a flash tank and purge columns of a polymerization reactor, wherein a stream containing solvent, polymer and unreacted monomers is flashed or otherwise treated to remove solvent or diluent and monomers therefrom. A first distillation column 1 realizes a rough cut between a mixture of diluent, co-monomer and the heavies, which exit as liquid bottom product 5. The heavy bottom product is further treated in a distillation column 3 and separated into three product streams: diluent vapor exiting as top product 22 is first cooled down in the overhead condenser 307 of the third distillation column. Then the stream 23 at the outlet of this condenser 307 is collected in a reflux drum 308 of the third distillation column 3. This reflux drum 308 is adapted to separate and collect the fully condensed stream 23. This liquid then exits the reflux drum 308 as liquid stream 24. The liquid stream 24 can be further split into a first liquid stream 26 which is sent as reflux to the third distillation column and a second liquid stream 25 which can be recycled to the first distillation column.

A purified liquid comonomer stream 21 is recovered from a tray just above the column sump and sent to storage for recycling to the polymerization reactor(s). The heavy components 20 are recovered from the column sump with the draining procedure being triggered on high column bottoms temperature.

The remaining monomer, diluent, with all light components, which exits from the top 6 of the first distillation column 1, is sent to a distillation column 2 as a vapor stream for further separation according to the process as described for FIG. 1. The stream will be condensed and separated at least twice in a condenser/separation cycle prior to entering said distillation second column 2 and treated in a same way as explained for FIG. 1. The distillation column 2 is used to generate four product streams: substantially pure diluent, so-called "substantially olefin-free" diluent is obtained as liquid bottom product 11. Light components such as formaldehyde, $H_2$, $N_2$, $O_2$, CO and $CO_2$ exit the distillation column 2 with olefin monomer and some residual diluent as a vapor stream 12, which according to an embodiment of the invention are further condensed before being further purified and separated in a monomer recovery unit represented by the box 19. Remaining diluent exits the column 2 as a liquid side stream 10. In addition, a separated side stream of diluent and monomer 9 is also recycled and re-used in a polymerization process.

This invention can be further illustrated by the following example of a preferred embodiment of the invention, although it will be understood that this example is included merely for purposes of illustration and are not intended to limit the scope of the invention unless otherwise specifically indicated.

EXAMPLE

This example illustrates the separation of a hydrocarbon-containing feed stream according to a process of the invention into a) a first side stream comprising isobutane and ethylene; b) a second side stream which is substantially hydrogen-free and comprises isobutane and ethylene, c) a bottom stream comprising substantially ethylene-free isobutane, and d) an overhead vapor stream comprising isobutane and ethylene and components such as formaldehyde, $H_2$, $N_2$, $O_2$, CO and $CO_2$. A recycling section according to an embodiment of the invention wherein such process is carried out is illustrated in FIG. 1. This recycling section setup can be used to recover a large part or most of the isobutane with minimized losses of ethylene.

In this example, the second side stream is drawn from the $6^{th}$ tray (counted from the top) of the second column. In such case it was calculated that a reboiler steam consumption of 800 kg/hour would be required and that the resulting total flow rate sent to the ERU would amount to some 325 kg/hour. These calculated values can be compared to conditions applied in a recycle system wherein no second side stream is separated, which means that line 10 is then absent and this flow rate then adds to the one exiting the column through line 11. In that later case steam flow rate reaches 1500 kg/hour and the flow rate to the ERU is above 700 kg/hour.

These values illustrate that separating a substantially hydrogen-free second side stream advantageously permits to strongly reduce the net requirement for ethylene-free isobutane (bottom stream). This makes it possible to reduce the steam consumption on the (second) distillation column, even by more than 700 kg/hour. In addition, this second side stream will take up some ethylene and will significantly reduce, preferably by more than 50%, the incondensable vapor stream still containing hydrogen that is removed from the separator of the second distillation column. Hence the loss of ethylene will be substantially reduced.

Table 1 given below compares the composition of a second side stream (nr. 10 in FIG. 1), separated in accordance with the present process, and as compared to a conventional side stream issued in a conventional recycling system.

TABLE 1

|  | Side stream according to the invention | Conventional side stream |
| --- | --- | --- |
| Hydrogen (ppm) | 0.33 | 318.54 |
| Ethylene (% wt) | 2.83 | 7.28 |
| Isobutane (% wt) | 97.16 | 92.65 |
| Hexene (ppm) | 0.02 | 0.02 |

As illustrated in Table 1, having an additional first side stream (9) permits to separate a second side stream (10) from an upper part of the distillation column comprising isobutane and ethylene, but which is substantially free of hydrogen. For comparison, in a conventional system, a side stream separated from a distillation column contains approximately similar amounts of isobutane and ethylene but contains much more hydrogen.

What is claimed is:

1. A process for recycling product streams separated from a hydrocarbon-containing feed stream comprising olefin monomer, one or more optional olefin co-monomer, hydrocarbon diluent and components selected from $H_2$, $N_2$, $O_2$, CO, $CO_2$, and formaldehyde, wherein said hydrocarbon-containing feed stream is separated by the steps of:
   a) introducing said hydrocarbon-containing feed stream into a first distillation column for subjecting said hydrocarbon-containing feed stream to distillation conditions adapted to remove:
      a1) a bottom stream comprising hydrocarbon diluent and one or more optional co-monomer, and
      a2) an overhead stream comprising hydrocarbon diluent, olefin monomer and components selected from $H_2$, $N_2$, $O_2$, CO, $CO_2$, and formaldehyde;
   b) condensing the overhead stream issued from the first distillation column in step a2) to form a first condensate and storing said first condensate in a first separator adapted to separate a first vapor stream and a first liquid stream;
   c) removing from said first separator said first vapor stream comprising olefin monomer, hydrocarbon diluent and components selected from formaldehyde, $H_2$, $N_2$, $O_2$, CO, and $CO_2$;
   d) condensing the first vapor stream removed in step c) to form a second condensate and storing said second condensate in a second separator adapted to separate a second vapor stream and a second liquid stream;
   e) removing from said second separator said second liquid stream of step d);
   f) separating said second liquid stream into a first side stream comprising hydrocarbon diluent and olefin monomer; and a remainder stream;
   g) introducing said remainder stream in a second distillation column and subjecting said remainder stream to distillation conditions adapted to remove:
      g1) a bottom stream comprising substantially olefin-free hydrocarbon diluent,
      g2) a substantially hydrogen-free second side stream comprising hydrocarbon diluent and olefin monomer, and
      g3) an overhead vapor stream comprising olefin monomer, hydrocarbon diluent and components selected from formaldehyde, $H_2$, $N_2$, $O_2$, CO, and $CO_2$,
   wherein said first side stream and said substantially hydrogen-free second side stream are recycled in a polymerization process for preparing bimodal polyolefin comprising at least two different polyolefin fractions that have been obtained in two different polymerisation reactors connected to each other in series, and wherein one of said polyolefin fractions has a higher molecular weight than said other polyolefin fraction, and
   wherein said substantially hydrogen-free second side stream is re-used in the polymerization process wherein the polyolefin fraction having the higher molecular weight is prepared, and wherein said first side stream is re-used in the polymerization process wherein the other polyolefin fraction is prepared.

2. The process according to claim 1, comprising the steps of:
   h) condensing the overhead vapor stream obtained in step g3), optionally in admixture of the first vapor stream removed in step c) to form condensate that is stored in the second separator; and
   i) subjecting the stored condensate obtained in step h) to steps e) to g).

3. The process according to claim 1, wherein said substantially hydrogen-free second side stream of step g2) comprises at least 2 wt % olefin monomer.

4. The process according to claim 1, wherein said substantially hydrogen-free second side stream of step g2) comprises at most 5 ppm by weight hydrogen.

5. The process according to claim 1, wherein said first side stream of step f) comprises less than 10 wt % olefin monomer.

6. The process according to claim 1, wherein said first side stream of step f) comprises less than 500 ppm by weight hydrogen.

7. The process according to claim 1, wherein said bottom stream comprising substantially olefin-free hydrocarbon diluent of step g1) comprises less than 5 ppm of olefin monomer and optionally less than 5000 ppm of olefin co-monomer.

8. The process according to claim 1, wherein said substantially hydrogen-free second side stream of step g2) is removed from an upper third of said second distillation column.

9. The process according to claim 1, wherein said bottom stream comprising substantially olefin-free hydrocarbon diluent of step g1) is re-used in a polymerization process for preparing bimodal polyolefin comprising at least two different polyolefin fractions that have been obtained in two different polymerisation reactors connected to each other in series, and wherein one of said fractions has a higher molecular weight than said other fraction, and wherein said bottom stream comprising substantially olefin-free hydrocarbon diluent is re-used in the polymerization process wherein the polyolefin fraction having the higher molecular weight is prepared.

10. The process according to claim 1, wherein the second vapor stream comprises olefin monomer, and components selected from formaldehyde, $H_2$, $N_2$, $O_2$, CO, and $CO_2$, and wherein the process further comprises recovering the olefin monomer from said second vapor stream.

11. The process according to claim 1, comprising introducing the bottom stream comprising hydrocarbon diluent and one or more optional co-monomer of step a1) in a third distillation column for subjecting said bottom stream comprising hydrocarbon diluent and one or more optional co-monomer to distillation conditions adapted to remove:
   1) a side stream comprising one or more optional co-monomer,
   2) an overhead stream comprising hydrocarbon diluent and optionally co-monomer, and
   3) a bottom stream comprising heavy components.

12. The process according to claim 1, wherein said hydrocarbon-containing feed stream comprising olefin monomer, one or more optional olefin co-monomer and hydrocarbon diluent is an effluent stream obtained from a polymerization process for preparing monomodal or bimodal polyolefin.

13. Use of a process according to claim 1 in a polymerization process for preparing bimodal polyolefin comprising at least two different polyolefin fractions that have been obtained in two different polymerisation reactors connected to each other in series, and wherein one of said fractions has a higher molecular weight, comprising the steps of:

feeding olefin monomer, a diluent, at least one polymerization catalyst, optionally hydrogen, and one or more optional olefin co-monomer(s) to a first reactor, polymerizing said olefin monomer in said first reactor to produce a polymer slurry comprising a first polyolefin fraction in the diluent, transferring said polymer slurry from said first reactor to a second reactor, feeding olefin monomer, a diluent, optionally hydrogen, and one or more optional olefin co-monomer(s) to said second reactor, polymerizing said olefin monomer and said one or more optional olefin co-monomer(s) in said second reactor to produce a slurry comprising a second polyolefin fraction in the diluent, said second polyolefin fraction having a different molecular weight than the polyolefin fraction produced in said first reactor, and discharging from said second reactor a slurry comprising bimodal polyolefin in said diluent, recovering bimodal polyolefin from the slurry by separating at least a majority of the diluent from the slurry in a hydrocarbon-containing feed stream, and subjecting said hydrocarbon-containing feed stream to a process according to claim 1.

14. The process according to claim 1, wherein said substantially hydrogen-free second side stream of step g2) comprises at least 3 wt % olefin monomer.

15. The process according to claim 1, wherein said substantially hydrogen-free second side stream of step g2) comprises at most 1 ppm by weight hydrogen.

* * * * *